(12) United States Patent
Herzberg et al.

(10) Patent No.: US 7,942,918 B2
(45) Date of Patent: May 17, 2011

(54) DEVICE FOR TREATING CARPAL TUNNEL SYNDROME

(75) Inventors: Uri Herzberg, Bridgewater, NJ (US); Robert Rousseau, Ottsville, PA (US); Ben Kibalo, Monmouth Junction, NJ (US); James Rudnick, Mahwah, NJ (US); Kevin Weadock, Hillsborough, NJ (US); Jessica Liberatore, Marlboro, NJ (US)

(73) Assignee: Ethicon, Inc., Somerville, NJ (US)

( * ) Notice: Subject to any disclaimer, the term of this patent is extended or adjusted under 35 U.S.C. 154(b) by 658 days.

(21) Appl. No.: 11/321,722

(22) Filed: Dec. 29, 2005

(65) Prior Publication Data
US 2007/0156158 A1 Jul. 5, 2007

(51) Int. Cl.
*A61F 2/06* (2006.01)
(52) U.S. Cl. .................................................. 623/1.12
(58) Field of Classification Search .......... 623/1.12, 623/1.15; 600/37; 606/151–155; 206/363, 206/438, 439
See application file for complete search history.

(56) References Cited

U.S. PATENT DOCUMENTS

| | | | | |
|---|---|---|---|---|
| 4,534,349 A | 8/1985 | Barrows | | 128/334 R |
| 4,669,474 A | 6/1987 | Barrows | | 128/334 C |
| 4,778,467 A | 10/1988 | Stensaas et al. | | 623/12 |
| 4,870,966 A | 10/1989 | Dellon et al. | | 128/334 R |
| 4,877,030 A * | 10/1989 | Beck et al. | | 606/195 |
| 4,920,962 A | 5/1990 | Proulx | | 606/152 |
| 5,011,486 A | 4/1991 | Aebischer et al. | | 606/152 |
| 5,026,373 A | 6/1991 | Ray et al. | | 606/61 |
| 5,423,804 A | 6/1995 | Kulick | | 606/14 |
| 5,466,215 A | 11/1995 | Lair et al. | | 602/21 |
| 5,954,765 A * | 9/1999 | Ruiz | | 623/1.15 |
| 6,042,605 A * | 3/2000 | Martin et al. | | 623/1.13 |
| 6,090,117 A | 7/2000 | Shimizu | | 606/152 |
| 6,146,419 A | 11/2000 | Eaton | | 623/11.11 |
| 6,171,338 B1 * | 1/2001 | Talja et al. | | 623/1.22 |
| 6,283,968 B1 | 9/2001 | Mehdizadeh | | 606/61 |
| 6,506,200 B1 | 1/2003 | Chin | | 606/190 |

(Continued)

FOREIGN PATENT DOCUMENTS
WO   WO 91/06261   5/1991

(Continued)

OTHER PUBLICATIONS

Ioannis V. Yannas and Brook J. Hill. "Selection of biomaterials for peripheral nerve regeneration using data from the nerve chamber model". Biomaterials. vol. 25, pp. 1593-1600, 2004.

(Continued)

*Primary Examiner* — Darwin P Erezo
*Assistant Examiner* — Son Dang

(57) ABSTRACT

A device for treating a patient having carpal tunnel disease includes a neural stent formed from an elastically deformable material or one that has shape memory properties. The neural stent is in the form of a mesh which, when implanted in a patient, curls about the median nerve below the transverse carpal ligament to separate the two and relieve pressure on the nerve caused by the carpal ligament.

15 Claims, 8 Drawing Sheets

U.S. PATENT DOCUMENTS

| | | | |
|---|---|---|---|
| 6,530,933 B1 | 3/2003 | Yeung et al. | 606/151 |
| 6,585,773 B1 | 7/2003 | Xie | 623/23.7 |
| 6,626,916 B1 | 9/2003 | Yeung et al. | 606/139 |
| 6,716,225 B2 | 4/2004 | Li et al. | 606/152 |
| 7,270,668 B2 * | 9/2007 | Andreas et al. | 606/108 |
| 2003/0204197 A1 | 10/2003 | Onyekaba et al. | 606/152 |
| 2004/0034407 A1 * | 2/2004 | Sherry | 623/1.15 |
| 2004/0199187 A1 | 10/2004 | Loughran | 606/152 |

FOREIGN PATENT DOCUMENTS

| | | |
|---|---|---|
| WO | WO 99/38453 | 8/1999 |
| WO | WO 00/10488 | 3/2000 |
| WO | WO 02/096300 | 12/2002 |

OTHER PUBLICATIONS

Serdar Tuzuner, M.D., Sibel Ozkaynak, M.D., Cem Acikbas, M.D., Aydin Yildirim, M.D., "Median Nerve Excursion During Endoscopic Carpal Tunnel Release". Neurosurgery. vol. 54, pp. 1155-1161, 2004.

Nordstrom DL, DeStefano F., Vierkant RA, Layde PM. "Incidence of diagnosed carpal tunnel syndrome in a general population". Epidemiology. May 1998, 9(3): 342-5.

Szabo RM. "Carpal tunnel syndrome as a repetitive motion disorder". Clin Orthop. Jun. 1998; (351): 78-89.

Nordstrom DL DeStefano F., Vierkant RA, Layde PM. "Incidence of diagnosed carpal tunnel syndrome in a general population". Epidemiology. May 1998, 9(3): 342-5.

* cited by examiner

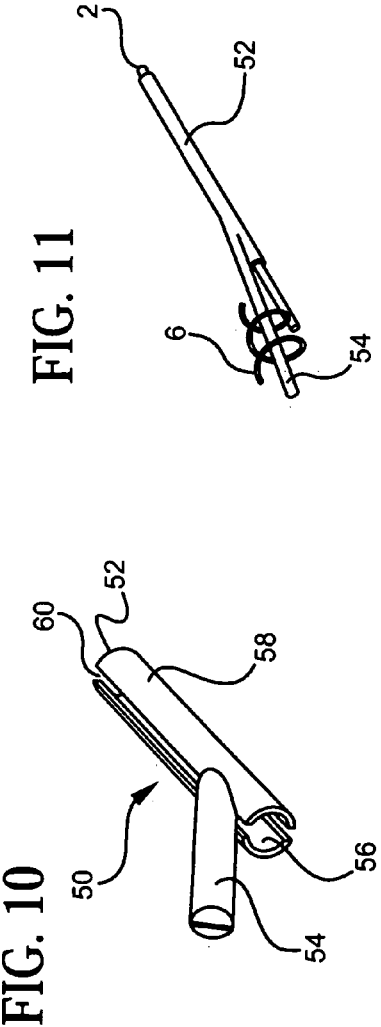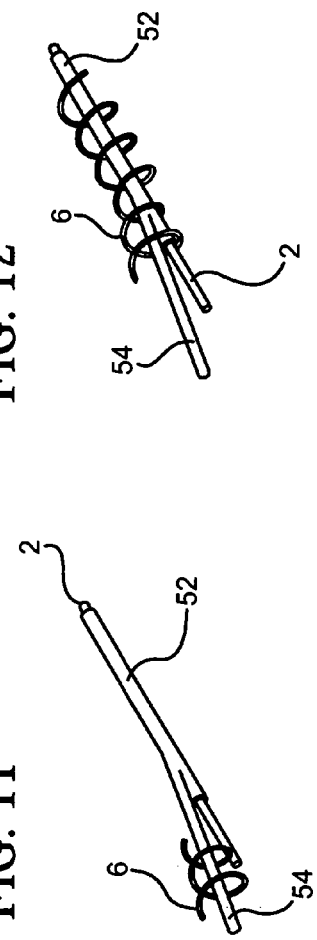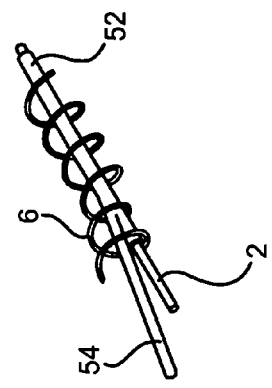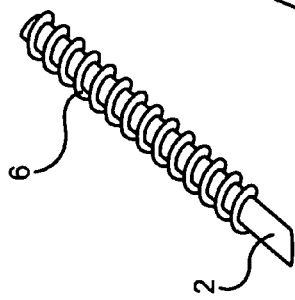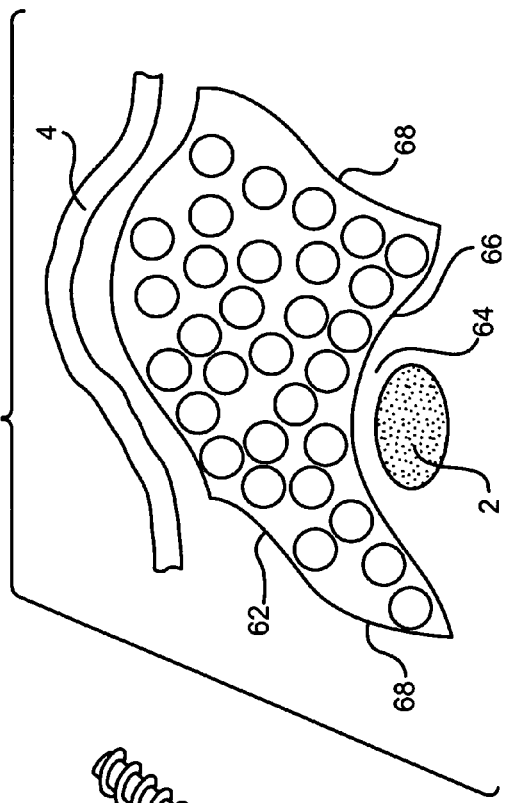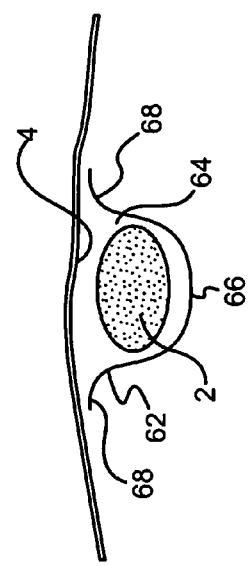

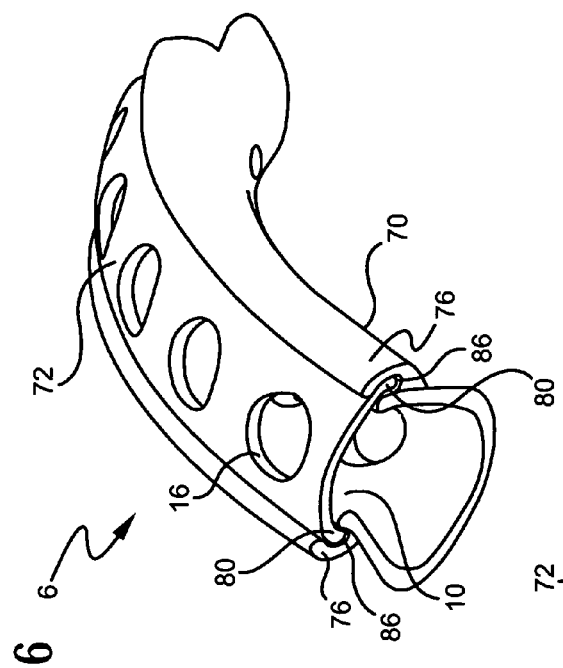
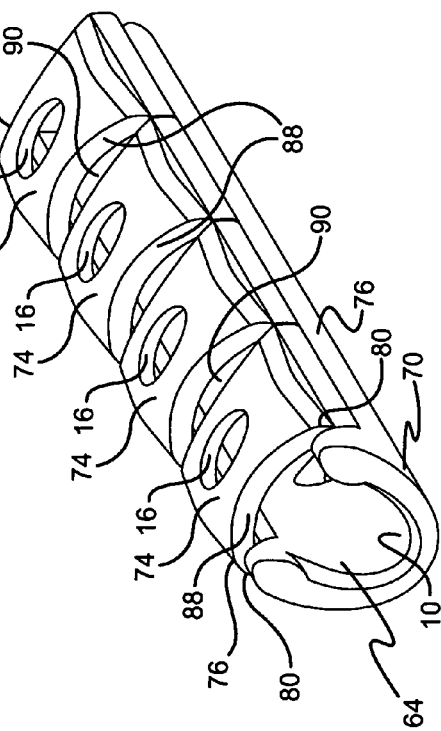
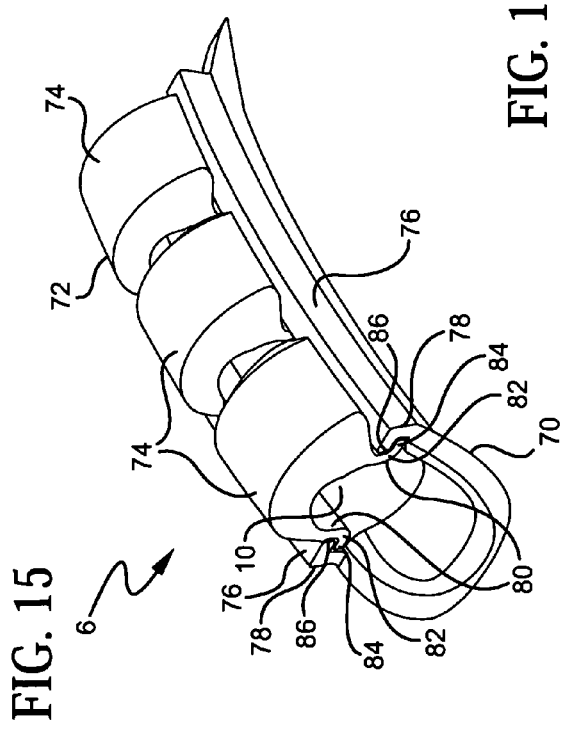

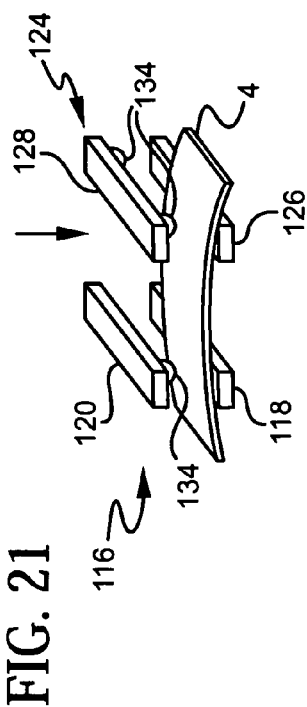
FIG. 21
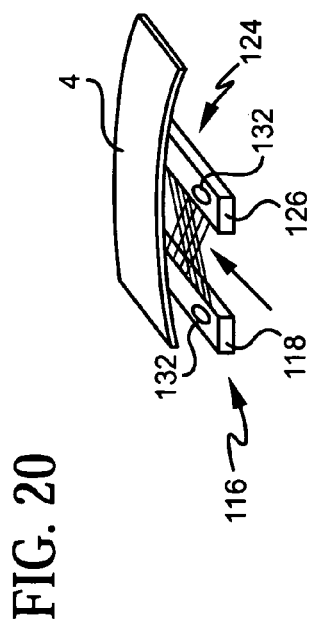
FIG. 20
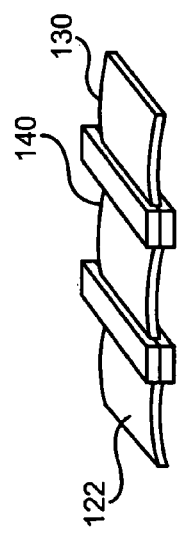
FIG. 23
FIG. 22
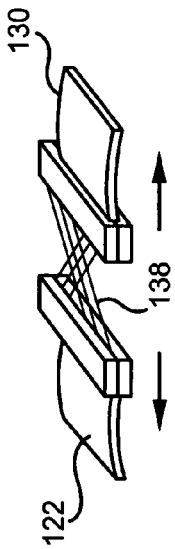
FIG. 24

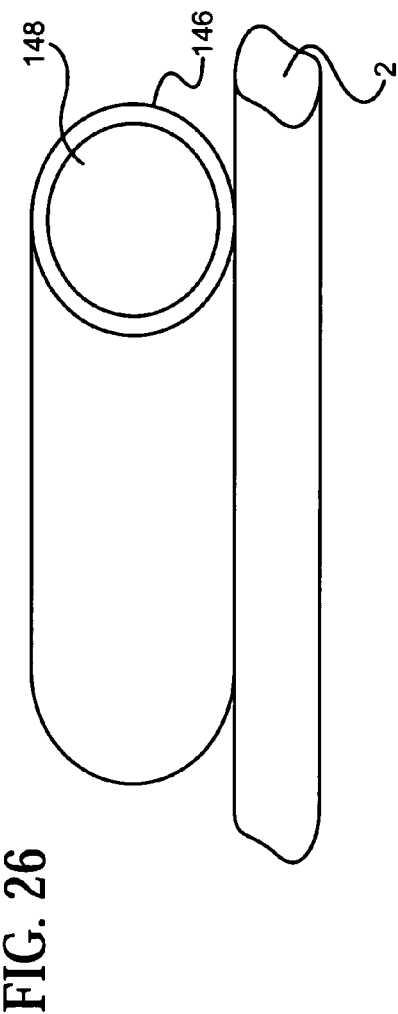
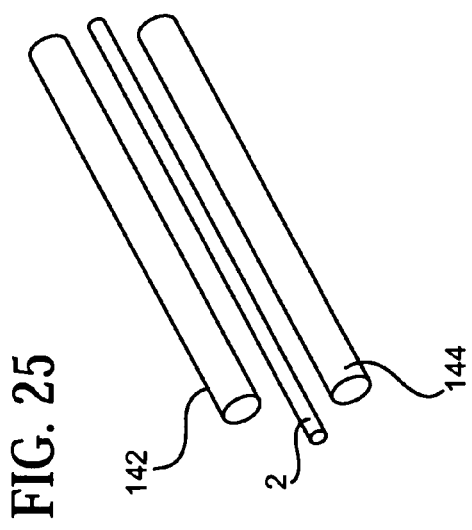
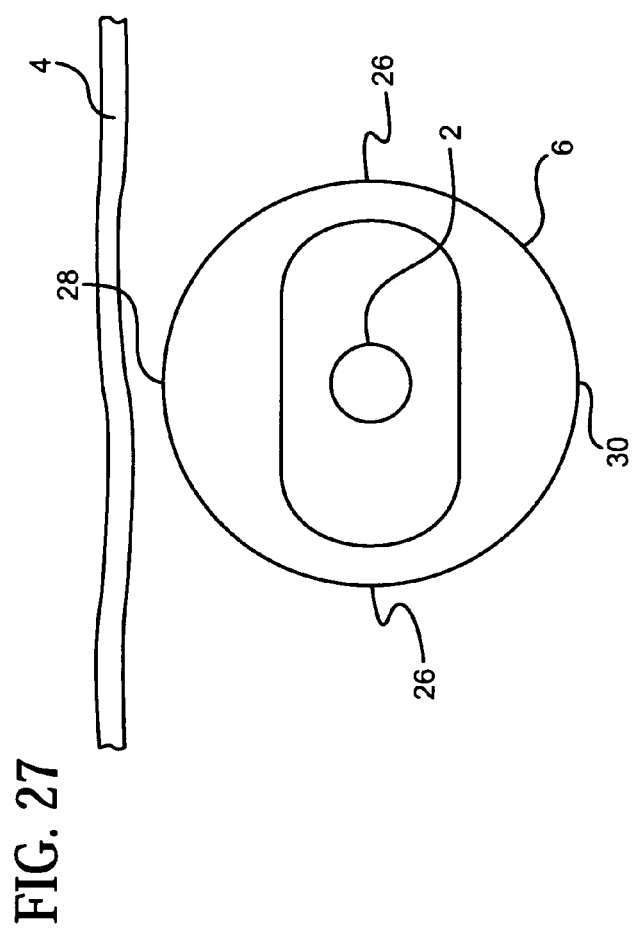

DEVICE FOR TREATING CARPAL TUNNEL SYNDROME

BACKGROUND OF THE INVENTION

1. Field of the Invention

This invention generally relates to methods and devices for treating nerve inflammation and damage in animals, including humans, and more particularly relates to methods and devices for treating carpal tunnel syndrome in humans.

2. Description of the Prior Art

Carpal tunnel syndrome is a condition that affects millions of people. In fact, the condition is the fastest growing condition among the list of repetitive motion disorders, which comprise over 48 percent of work related diseases in accordance with the teachings of R. M. Szabo in the article, "Carpal Tunnel Syndrome as a Repetitive Motion Disorder", Clin. Orthop., 1998 June; (351): 78-89. The condition prevalence is approximately 3.5 cases per 1000 persons per year, as taught by D. L. Nordstrom et al. in the article, "Incidence of Diagnosed Carpal Tunnel Syndrome in a General Population", Epidemiology, 1998 May; 9(3): 342-5.

Carpal tunnel syndrome arises from pinching or compression of the median nerve by the transverse carpal ligament and possibly the hypertrophied tenosynovium that forms the inner lining of the carpal canal. This nerve runs in the carpal tunnel, which is on the palmar side of the hand, with the ligament on top of it. The ligament holds the carpal bone together, providing stability to the hand, as shown in FIG. 1 of the drawings.

Following compression of the nerve, tingling, weakness, incoordination and pain, which is described by those afflicted as "needles and pins", are the end result. During the early stages of the disease, anti-inflammatory drugs and modification of the behaviors or activities that lead to the disease are often prescribed. Still, most patients seek help only when the condition has worsened, and muscle atrophy and severe pain are possible. If the condition is left untreated, permanent nerve damage could be taking place.

The most common surgical intervention for this disease is to alleviate the pressure on the median nerve by releasing it from the transverse carpal ligament. This is done by open or endoscopic surgery, where the carpal ligament is incised. More specifically, in an open procedure, the skin and connected tissue above the ligament are incised, or with endoscopy, where a small incision is made at the wrist through which an endoscope is inserted. In both approaches, the median nerve is isolated and separated from the carpal ligament. The ligament is then incised and the pressure is relieved from the median nerve.

Several complications are associated with the surgery. The healing time can be prolonged, a second surgery may be necessary to dissect the ligament adhesions of the cut edges of the ligament to the nerve and surrounding tissues can further complicate the situation. Also, the inflammatory reaction to the dissected ligament can be severe. It should be realized that any time a tissue is cut, the surgeon risks cutting the wrong tissue. In addition, when the ligament is cut, a soft tissue structure that provides support to the hand's bony structure is lost, resulting in less support and stability of the hand.

OBJECTS AND SUMMARY OF THE INVENTION

It is an object of the present invention to provide a device for treating patients with nerve injury or damage who are suffering from a repetitive motion disorder.

It is another object of the present invention to provide a device for treating patients with carpal tunnel syndrome.

It is still another object of the present invention to provide a method for surgically implanting a device for treating patients who have nerve injury or damage and who suffer from a repetitive motion disorder.

It is yet a further object of the present invention to provide a device, and method for implanting such a device, for treating carpal tunnel syndrome which avoids the complications and detrimental effects associated with known surgical procedures for treating carpal tunnel syndrome.

It is still a further object of the present invention to provide a device for protecting the median nerve of a patient suffering from carpal tunnel syndrome, which device is relatively easily implantable.

In accordance with one form of the present invention, a device for treating patients with carpal tunnel syndrome is in the form of a stent which protects the median nerve and separates it from the transverse carpal ligament. The stent may be in the form of a mesh made from an absorbable material or a non-absorbable material which preferably is lubricious on its inside surface which faces the median nerve and has barbs or other anchoring means on its outside surface to prevent it from moving from its surgically implanted site. The stent allows the median nerve to heal and return to full function without the need to incise the transverse carpal ligament, which is the current standard of care for treating carpal tunnel syndrome.

The stent may be formed with a "C"-shape in transverse cross-section to allow the insertion of the median nerve within the channel thus formed by the stent, or may have elastically deformable properties, such as with elastomers or rubbers which, when inserted in proximity to the median nerve and released from a particular shape, will close surrounding the nerve to protect it. In another form of the present invention, the stent may be formed from two or more mating pieces which are assembled in situ to surround and protect the nerve from the ligament. The device may also be made to release drugs, such as anti-inflammatory drugs, anti-proliferative drugs, analgesics and anesthetics. Additional devices for treating patients having carpal tunnel syndrome or suffering from other repetitive motion disorders, formed in accordance with the present invention, and methods of implanting such devices, are described in greater detail in the section, "Detailed Description of the Preferred Embodiments".

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 10 is a perspective pictorial illustration of apparatus of the present invention for implanting the device of the present invention shown in FIG. 9 in a patient's body.

FIG. 11 is a perspective pictorial illustration of the apparatus of the present invention shown in FIG. 10 being used to implant the device of the present invention shown in FIG. 9 in a patient's body in a first stage of a method of implanting the device.

FIG. 12 is a perspective pictorial illustration of the apparatus of the present invention shown in FIGS. 10 and 11 being used to implant the device of the present invention shown in FIG. 9 in a patient's body in a second stage of a method of implanting the device.

FIG. 12A is a perspective pictorial illustration of the device of the present invention shown in FIG. 9 implanted in the patient's body about a nerve after the apparatus of the present invention shown in FIGS. 10 through 12 is removed therefrom.

FIG. 13 is a pictorial illustration of a device for treating a patient with carpal tunnel disease or other nerve injury formed in accordance with a third form of the present invention, and illustrating the positioning of the device in the patient's body.

FIG. 14 is a pictorial illustration of the device of the present invention shown in FIG. 13 implanted in a patient's body in a different manner from that shown in FIG. 13.

FIG. 15 is a perspective view of a device for treating a patient with carpal tunnel disease or other nerve injury formed in accordance with a fourth form of the present invention.

FIG. 16 is a perspective view of a device for treating a patient having carpal tunnel disease or other nerve injury formed in accordance with a fifth form of the present invention.

FIG. 17 is a perspective view of a device for treating a patient having carpal tunnel disease or other nerve injury formed in accordance with a sixth form of the present invention.

FIG. 20 is a perspective pictorial illustration of a device for treating a patient having carpal tunnel disease formed in accordance with a ninth form of the present invention, where the carpal ligament is transected, and illustrating a first stage in a method of implanting the device in a patient's body.

FIG. 21 is a perspective pictorial illustration of the device of the present invention shown in FIG. 20, illustrating a second stage in the method of implanting the device in a patient's body.

FIG. 22 is a perspective pictorial illustration of the device of the present invention shown in FIGS. 20 and 21, illustrating a third stage in the method of implanting the device in a patient's body.

FIG. 23 is a perspective pictorial illustration of the device of the present invention shown in FIGS. 20 through 22 and illustrating a fourth stage in the method of implanting the device in a patient's body.

FIG. 24 is a perspective pictorial illustration of the device of the present invention shown in FIGS. 20 through 23 and illustrating the device implanted in a patient's body and the functioning of the device.

FIG. 25 is a perspective view of a device for treating a patient having carpal tunnel disease or other nerve injury formed in accordance with a tenth form of the present invention.

FIG. 26 is a perspective view of a device for treating a patient having carpal tunnel disease or other nerve injury formed in accordance with an eleventh form of the present invention.

FIG. 27 is a transverse cross-sectional view of a device for treating a patient having carpal tunnel disease or other nerve injury formed in accordance with a twelfth form of the present invention.

DETAILED DESCRIPTION OF THE PREFERRED EMBODIMENTS

Figure 1:
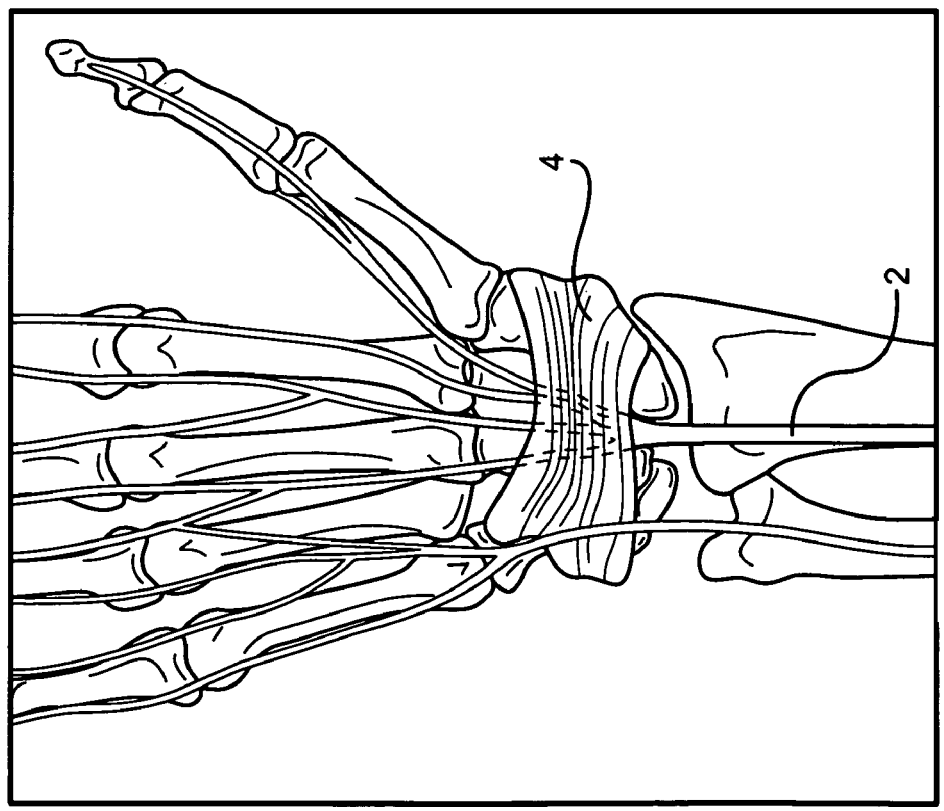
FIG. 1 is a pictorial illustration of a human hand to show the location of the transverse carpal ligament and the median nerve.

In order to facilitate an understanding of the use and structure of the present invention for treating carpal tunnel disease and other nerve injuries, reference should be initially made to FIG. 1 of the drawings, which shows the location of the median nerve 2 with respect to the transverse carpal ligament 4 in a patient's wrist. In particular, carpal tunnel syndrome or disease is a condition which arises from pinching or compression of the median nerve 2 by the transverse carpal ligament 4. This nerve runs in the carpal tunnel, which is on the palmar side of the hand, with the ligament on top of it. The ligament holds the carpal bone together, providing stability to the hand. Hypertrophy of the tenosynovium, which is the inner lining of the carpal canal, can further exert pressure on the nerve.

Compression of the nerve 2 by the carpal ligament 4 may result in tingling, weakness, incoordination and pain. During the early stages of the disease, anti-inflammatory drugs and modifications of the behaviors or activities that lead to the disease are often prescribed. Still, most patients seek help only when the condition has worsened and muscle atrophy and severe pain are present. Often, surgical intervention is necessary, and this should be initiated as soon as possible. If the condition is left untreated, permanent nerve damage could be taking place. The device of the present invention aids in relieving pressure and compression on the nerve 2 by the carpal ligament 4, allowing the nerve to heal. Where surgical intervention is necessary, and the carpal ligament 4 is transected, the device of the present invention, in another form, not only protects the median nerve 2, but also holds the transected ends of the carpal ligament 4 together so that the ligament continues to provide support and stability to the patient's hand. This device also prevents the cut ligament edges from adhering to the nerve.

In accordance with one form of the present invention, and now referring to FIGS. 2-5 of the drawings, it will be seen that a device for treating a patient having an injury to or inflammation of a nerve, such as a result of carpal tunnel disease, includes a neural stent 6. The neural stent 6 is at least generally in the form of a cylindrical tube, having a tubular body 8 in which is formed a bore 10 running axially therethrough for receiving and protecting the inflamed or injured nerve. Preferably, the stent 6 includes an outer wall 12 for at least partially surrounding the inflamed or injured nerve, and a slot 14 formed in the thickness of the outer wall 12 and extending axially there along. The slot 14 is in communication with the axial bore 10 for receiving therethrough the inflamed or injured nerve.

The stent 6 may be formed at least partially from a material which is absorbable by a patient's body. Alternatively, the stent 6 may be formed at least partially from a material which is not absorbable by a patient's body. Various absorbable and non-absorbable materials may be used to form the stent, as is well known in the art. Such non-absorbable materials for forming the neural stent 6 may include, but are not limited to, polypropylene, nylon, polyester, stainless steel, Nitinol and nickel-titanium alloys, and others. Absorbable materials for forming the neural stent 6 may include, but are not limited to, polylactone, poly lactic acid (PLA), polyglycolic acid (PGA), polydioxanone and polylactide-co-glycolide (PLGA). The absorbability or biodegradability of the materials used for forming the stent 6 may be chosen to provide a varying degree of absorbability by the body over time such as anywhere from a few days to several years, in order to provide sufficient time for the median nerve 2 or other nerve to heal.

As also shown in FIGS. 2-5 of the drawings, the outer wall 12 of the neural stent 6 may be formed as a mesh to allow the passage of fluids therethrough and into the axial bore 10 of the stent. Also, the mesh may permit tissue in growth in order to anchor the stent 6 in place at the implantation site about the median nerve 2 or other nerve.

Alternatively, the outer wall 12 of the stent may include a plurality of openings 16 (see FIG. 16) formed through the thickness thereof, the openings 16 communicating with the axial bore 10 of the stent so as to allow the passage of fluids through the openings and into the axial bore and, optionally, to allow tissue in growth to anchor the stent 6 in the patient's body. By making the device from a mesh-like structure, the mesh will embed itself in the carpal ligament 4 above the median nerve 2 and the tissue below the nerve while alleviating the pressure and protecting the nerve from the pressure exerted by the transverse carpal ligament 4. Also, by being made from a mesh material, the neural stent 6 will be anchored in the tissue so that there is minimal chance of the device turning around and pressing on the median nerve 2.

Also, preferably, the neural stent 6 may include a plurality of tissue anchors formed on the outer surface thereof. Such tissue anchors may be in the form of barbs 18 which extend outwardly from the outer surface of the neural stent outer wall 12. Preferably, the barbs 18 are situated on the palmar side of the stent. The barbs 18 will engage the tissue and/or ligament below and above the median nerve 2 to help hold the neural stent 6 in place at the implantation site.

The inner surface of the outer wall 12 of the neural stent 6, which is opposite the outer surface and which faces the bore 10 that receives the inflamed or damaged nerve, may be coated with a substance that makes the inner surface lubricious to allow movement of the nerve 2 within the bore when the patient's palm is extended or flexed. Examples of lubricious biomaterials and substances which may be used for the stent include, but are not limited to PTFE (polytetrafluoroethylene), silicone, silicone rubber, polyurethane, as well as plasma coated surfaces. Various hydrogels can also be considered, and those include, but are not limited to, alginate, self assembling peptides, hyaluronic acid based polymers, collagen based polymers, silicone based polymers, and oxidized regenerated cellulose.

Again referring to FIGS. 2-4 of the drawings, it can be seen that the neural stent 6 includes a main body 20, a first open axial end 22 and a second open axial end 24 situated opposite the first open axial end 22, with the main body 20 being interposed therebetween. At least one, but preferably both, of the first open axial end 22 and the second open axial end 24 may be flared so that one or both of the axial ends have a diameter which is greater than that of the main body 20 of the neural stent 6.

Figure 2:
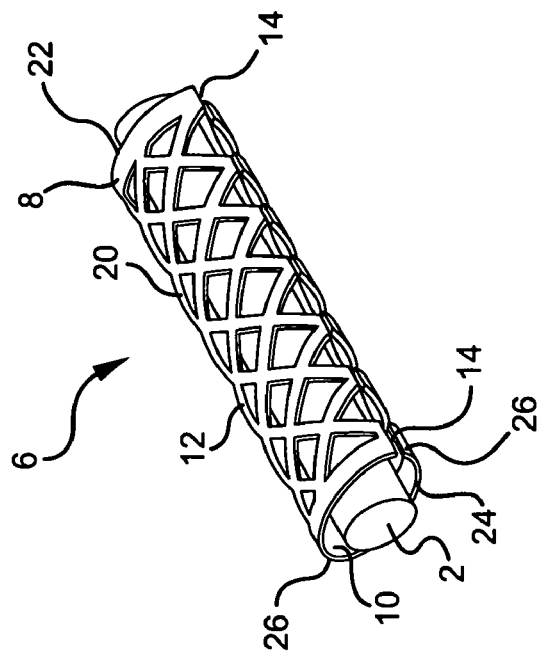
FIG. 2 is a perspective view of a device for treating carpal tunnel disease or other nerve injury formed in accordance with one form of the present invention.
Figure 3:
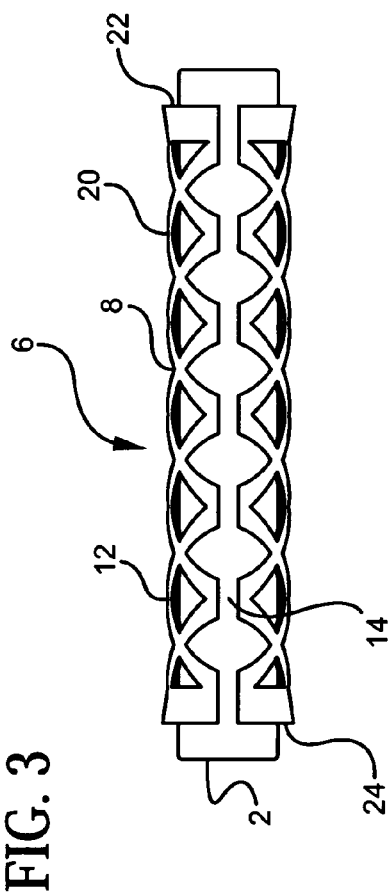
FIG. 3 is a side view of the device of the present invention shown in FIG. 2 for treating carpal tunnel disease or other nerve injury.
Figure 4:
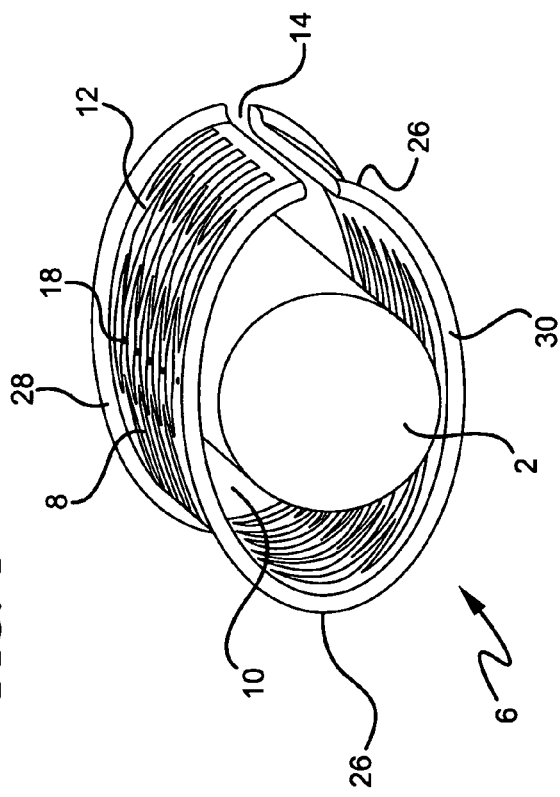
FIG. 4 is a perspective view of the device of the present invention shown in FIGS. 2 and 3.
Figure 5:
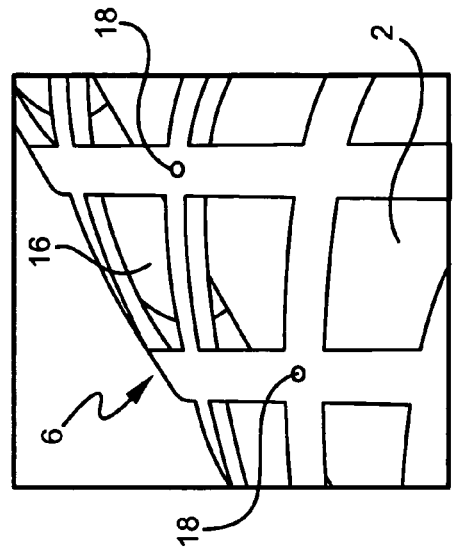
FIG. 5 is a detailed perspective view of a portion of the device of the present invention shown in FIGS. 2 through 4.

Thus, as shown in FIGS. 2-4 of the drawings, the stent 6 has a "C" shape in transverse cross-section and, preferably, it has enough flexibility and deformability such that it closes around the median nerve 2 to protect it on all sides when implanted in the patient's body. The thickness of the outer wall 12 of the neural stent 6 may be uniform circumferentially about the stent, or alternatively, the lateral sides 26 of the stent may be made more pliable than the dorsal and ventral sides 28, 30, respectively (i.e., top and bottom sides), when viewing the stent implanted in the patient's body, such as shown cross-sectionally in FIG. 27 of the drawings, where the dorsal side 28 and ventral side 30 are made stiffer to resist pressure from the transverse carpal ligament 4 on the median nerve 2. Such may be accomplished by making the thickness of the outer wall 12 of the neural stent at the dorsal and ventral sides 28, 30 thicker than at the lateral sides 26, such as shown in FIG. 27.

Preferably, the stent 6 is long enough to protect the median nerve 2 from the transverse carpal ligament 4, but short enough such that it does not impede blood flow and motion of the hand. Even more preferably, the neural stent 6 is between about 0.5 inches and about 2.5 inches in length, with the inside surface of the outer wall 12 defining an axial bore 10 with a diameter of about 1.5 inches. Also, the slot 14 formed axially along the length of the outer wall 12 is preferably about 2 millimeters to about 8 millimeters in width to allow the median nerve to freely pass therethrough and into the axial bore 10 of the neural stent 6 when the stent is implanted in the patient's body.

As mentioned previously, the neural stent 6 may include a plurality of tissue anchors, such as barbs 18, formed on the outer surface of the stent outer wall 12. Alternatively, or in addition to having barbs 18 on the neural stent, the device may include other tissue anchors which extend axially either from one or both of the first and second open axial ends 22, 24 of the neural stent 6. Such tissue anchors may be, for example, hooks 32 (see FIG. 6) joined to sutures which, in turn, are joined to the neural stent at the first and/or second open axial end 22, 24 of the stent. The hooks 32 are further provided to help secure the stent 6 in place between the transverse carpal ligament 4 and the median nerve 2 during the surgical procedure to implant the neural stent in the patient's body.

Figure 6:
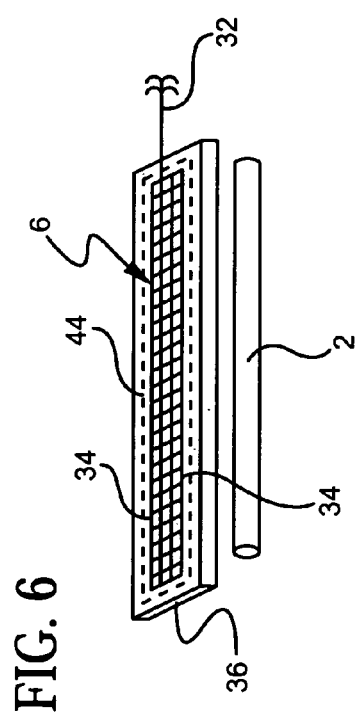
FIG. 6 is a perspective pictorial illustration of apparatus for implanting in a patient's body the device of the present invention shown in FIGS. 2 through 5, and illustrating a first stage of a method of implanting the device between the transverse carpal ligament and the median nerve of a patient.

Referring again to FIGS. 2-5 of the drawings, preferably the neural stent 6 may be formed of an elastically deformable material, such as certain polymers and elastomers which are well known to those skilled in the art, or a deformable material having shape memory properties, such as the alloy Nitinol. Formed of such materials, the neural stent 6 is deformable between a first shape, for example where the neural stent is in a generally planar form having opposite lateral edges 34, such as shown in FIG. 6 of the drawings, and a second shape in which the neural stent 6 is in a generally cylindrical form and where the lateral edges 34 of the material face each other and define therebetween the slot 14 that communicates with the axial bore 10 and which is provided for receiving therethrough the median nerve, or alternatively, where the lateral edges 34 overlap one another so that stent 6 curls around and completely encircles the median nerve 2. A neural stent 6 in this second shape is shown in FIG. 8 of the drawings.

Figure 7:
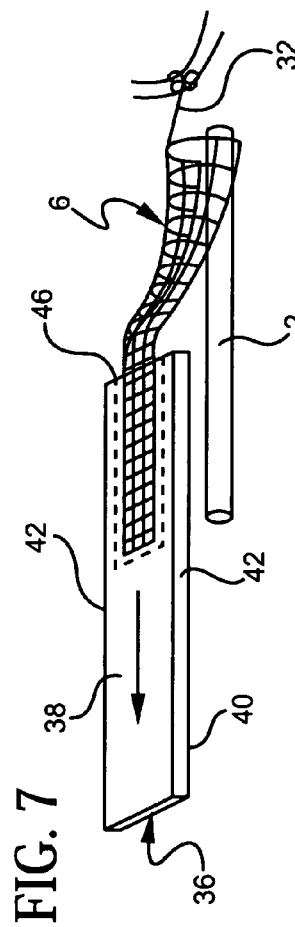
FIG. 7 is a perspective pictorial illustration of the apparatus of the present invention shown in FIG. 6 in a second stage of deploying or implanting the device of the present invention shown in FIGS. 2 through 5 in a patient's body.
Figure 8:
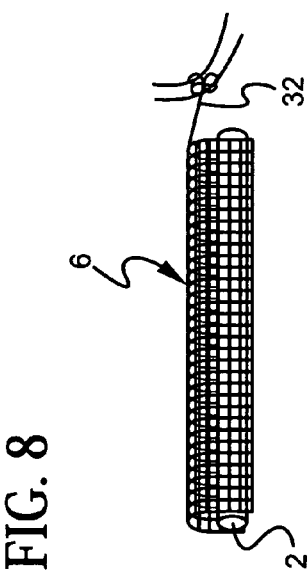
FIG. 8 is a perspective pictorial illustration of the apparatus of the present invention shown in FIGS. 6 and 7 in a third stage of deploying or implanting the device of the present invention shown in FIGS. 2 through 5 in a patient's body.

Referring to FIGS. 6-8 of the drawings, apparatus for implanting a device for treating a patient having carpal tunnel disease or other nerve injury, such as the device shown in FIGS. 2-5 or a device that is made from an elastically deformable material or one that has shape memory properties, as well as a method of implanting such a device in a patient, are illustrated. More specifically, a rigid stent delivery envelope 36 which at least has a top wall 38 and a bottom wall 40 opposite the top wall 38, but may include lateral side walls 42 and may be formed having an elongated box-like shape is used to implant the neural stent 6 in a patient's body. The top and bottom walls 38, 40 define therebetween a pocket 44 for housing the neural stent when the stent has a generally planar form and is in its first shape described previously. The rigid stent delivery envelope 36 further includes an open end 46 between the top and bottom walls 38, 40, which open end 46 defines an opening communicating with the pocket 44 and through which the neural stent 6 may pass.

As shown in FIG. 6 of the drawings, the rigid stent delivery envelope 36 is placed into the carpal tunnel in close proximity to the median nerve 2 and, more specifically, between the carpal ligament 4 and the median nerve. It houses the stent in its flattened shape, and prevents it from curling into a tubular shape due to the narrow confines of the delivery envelope which has a depth between the top and bottom walls 38, 40 that is preferably only slightly greater than the thickness of the stent in its flattened condition.

A separate tool (not shown), or one which is affixed to the envelope, may be used to retract tendons and blood vessels or other tissues in close proximity to the median nerve 2 when positioning the envelope 36 in place between the median nerve 2 and the carpal ligament 4. Such a tool would include an end shaped similar to a plow head or a wedge-like device to retract these tissues. The use of such a tool would effectively prevent pinching the nerves, tendons, and blood vessels at the surgical site during the delivery of the stent.

A tissue anchor 32, such as that described previously, attached to the forward axial end 22 of the stent is caused to engage tissue distal to the carpal tunnel. The anchor 32, which is firmly attached to the stent, holds the stent over the median nerve 2 as the envelope 36 is removed from the patient's body. This causes the neural stent 6 to be withdrawn from the rigid delivery envelope 36 and to be released from the constrained flattened shape it is in when housed by the rigid delivery envelope 36, and further allows the stent to deform to its curled, cylindrical shape to encircle the median nerve 2 due to its elasticity or shape memory properties, as shown in FIG. 7.

FIG. 8 shows the envelope 36 entirely removed from the surgical site and the stent 6 fully delivered and situated in place, encircling the median nerve 2 and protecting the median nerve from further damage. The tissue engaging anchors or the barbs 18 formed on the outer surface of the outer wall 12 hold the stent in place between the median nerve 2 and the transverse carpal ligament 4. Other tissue anchors, such as the previously mentioned hooks 32 and sutures extending and affixed to the opposite rearward axial end 24 of the stent, may be used to further secure the stent in its proper position over the nerve and between the nerve and the carpal ligament.

It should be realized that the neural stent 6 need not fully encircle the median nerve 2 to protect it from damage. As will be described in greater detail, the stent may be U-shaped to exert force on the carpal ligament 4 to separate it from the median nerve below it.

Figure 9:
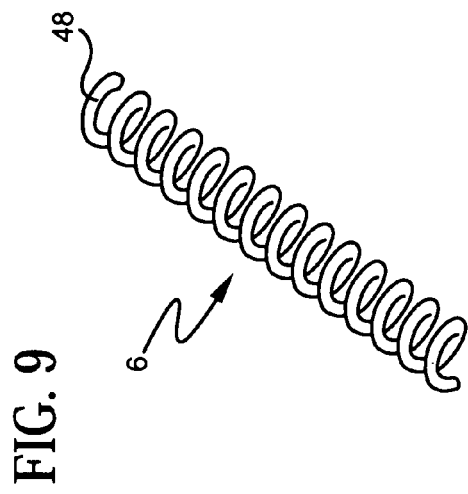
FIG. 9 is a perspective view of a device for treating carpal tunnel disease or other nerve injury formed in accordance with a second form of the present invention and situated about a nerve.

FIG. 9 illustrates another form of the present invention, that is, a device for treating a patient having carpal tunnel disease or other injury to a nerve. In this embodiment of the present invention, the neural stent 6 is formed as a spiral winding 48 defining an axial bore 10 for receiving and protecting the inflamed or injured nerve. Preferably, adjacent wraps of the spiral winding 48 are separated from each other to define an open space therebetween which communicates with the internal axial bore 10 and allows fluids to pass into the bore in which the nerve 2 is situated after the device is implanted in a patient's body.

Referring now to FIGS. 10-12A of the drawings, apparatus for implanting such a spirally wound neural stent, and a method for implanting such a stent, in accordance with the present invention, are illustrated. More specifically, an apparatus for delivering a spirally wound neural stent 6, such as shown in FIG. 9 of the drawings, preferably includes a generally Y-shaped structure 50 having a first leg 52 and a second leg 54 attached to the first leg 52 and extending angularly therefrom. The first leg 52 is generally in the form of a cylindrical tube having a bore 56 formed axially therethrough for selectively receiving the median nerve 2. The first leg 52 further has an outer wall 58 and a slot 60 formed through the thickness of the outer wall 58 which extends axially along the first leg. The slot 60 is in communication with the bore 56 so that it may receive through it the nerve 2 and so that the nerve may be temporarily positioned within the axial bore of the first leg 52 during the surgical implantation of the neural stent.

The second leg 54 is generally in the form of a rod, which is herein understood to include a tube-like structure like the first leg 52, with or without a bore, or thus may be solid through its thickness. The rod has an outer diameter which is preferably less than the inner diameter of the neural stent 6 defined by the spiral winding 48 so that the neural stent may be positioned on the second leg 54 and rotatable thereon. The spirally wound neural stent 6 is transferable from the second leg 54 to the first leg 52 by rotating the neural stent in at least one direction, such as clockwise as shown in FIGS. 11 and 12, for a stent that is wound in a clockwise direction, such as shown in FIG. 9.

Preferably, in order to implant the neural stent 6 having the spiral winding 48 such as shown in FIG. 9, using the preferred apparatus shown in FIG. 10, the apparatus is positioned in a patient's body under the transverse carpal ligament 4 such that the median nerve 2 thereunder passes through the slot 60 formed in the first leg 52 and into the axial bore 56 of the first leg.

The neural stent 6, which is wound about the second leg 54, is then rotated on the second leg so that its leading free end passes from the second leg to the first leg 52 and begins to wrap around the first leg, as illustrated in FIGS. 11 and 12 of the drawings. The neural stent 6 is continued to be rotated until it is fully transferred from the second leg 54 to the first leg 52 which contains the median nerve 2 within its axial bore 56.

After the neural stent is completely advanced from the second leg 54 to the first leg 52 by rotation of the stent, the apparatus is removed from the patient's body by sliding the first leg 52 backwardly away from the transverse carpal ligament 4. The stent may be anchored to surrounding tissue or may be physically or mechanically forced by the surgeon from the first leg 52 as the apparatus is removed, leaving the neural stent 6 situated alone and in place encircling the median nerve 2 and under the carpal ligament 4, as shown in FIG. 12A of the drawings.

As mentioned previously, the device of the present invention for treating a patient suffering from carpal tunnel syndrome or other nerve damage does not necessarily need to include a neural stent that entirely encircles the median nerve. Alternatively, and as shown in FIGS. 13 and 14 of the drawings, the device may include a U-shaped neural stent or shield 62. More specifically, the neural stent or shield 62 is in the form of an elongated member which is generally U-shaped in transverse cross-section to define a channel 64 for receiving and protecting the median nerve 2 of a patient. The neural shield 62 may be formed from a mesh material, or may have openings formed through the thickness thereof to allow the flow of fluid therethrough to the median nerve 2 situated in the channel.

The neural shield 62 is implantable in a patient being treated for carpal tunnel syndrome and is positioned between the carpal ligament 4 and the median nerve 2 of a patient to separate the two to prevent the ligament from compressing the nerve. The neural stent or shield 62 includes a U-shaped middle section 66 and opposite lateral edges 68 joined to the middle section 66, where the U-shaped middle section 66 defines the channel 64 for receiving and protecting the median nerve of a patient. As shown in FIG. 13, the neural stent or shield 62 is implanted in the patient and disposed such that the U-shaped middle section 66 engages and supports the transverse carpal ligament 4, with the median nerve 2 lying thereunder within the channel 64 of the neural shield. Alternatively, and as shown in FIG. 14 of the drawings, the neural shield 62 may be disposed such that the opposite lateral edges 68 engage the transverse carpal ligament 4 of the patient to separate the carpal ligament from the median nerve 2 so that the ligament no longer exerts pressure on the nerve when the neural shield is implanted in the patient. The median nerve 2 lies within and is protected by the channel 64 defined by the U-shaped middle section 66 of the neural shield.

FIGS. 15-17 illustrate further embodiments of the device of the present invention to treat a patient having carpal tunnel disease or other nerve injury. In particular, and as shown in FIG. 15, the device of the present invention includes a neural stent 6 having a bottom axially elongated member 70 and a top axially elongated member 72, the top axially elongated member 72 being formed from one piece or several pieces 74 arranged axially side-by-side across the bottom elongated member 70. The bottom and top elongated members 70, 72 are joined together to define the neural stent 6 with a generally cylindrical shape having an axial bore 10 therein for receiving and protecting the inflamed or injured nerve. The top and bottom elongated members 70, 72 are generally U-shaped in transverse cross-section to define the bore 10 for receiving and protecting the injured nerve.

As shown in FIG. 15, the bottom elongated member 70 preferably includes lateral edges 76 from which upwardly extend L-shaped flanges 78 extending axially along the length thereof. The top elongated member 72, either integrally formed or formed in separate pieces 74, also includes opposite lateral edges 80 from which project L-shaped flanges 82 which are shaped complementary to the L-shaped flanges 78 of the bottom elongated member 70. The end legs 84 of the L-shaped flanges 82 of the top axially elongated member 72 are received in respective channels 86 defined by the L-shaped flanges 82 of the bottom elongated member 70 so that the end legs 84 of the top elongated member 72 may be resiliently snap-fitted in, or slidably received by, the channels 86 of the bottom elongated member 70 to secure the top and bottom elongated members together.

Accordingly, the bottom U-shaped elongated member 70 may be positioned under the median nerve 2, with the median nerve received between the lateral edges 76 of the bottom member and cradled by the bottom member 70, and the neural stent 6 may be assembled in situ by sliding or snap-fitting the top elongated member 72 onto the bottom elongated member 70, the two members defining together the axial bore 10 in which the median nerve 2 is situated and protected. The top elongated member 72 is, therefore, situated between the median nerve 2 and the transverse carpal ligament 4. To facilitate assembly of the neural stent during the surgical implantation of the stent, the top elongated member 72 may be formed of a plurality of separate pieces 74, as shown in FIG. 15 and as described previously, each of which may be individually snap-fitted or slid into the channels 86 of the L-shaped flanges 78 of the bottom elongated member 70 to secure the separate pieces 74 defining the top elongated member 72 to the bottom elongated member 70. It should be further noted from FIG. 15 that the bottom elongated member 70 may be arched, if desired, to conform to the shape of the patient's palm and to provide greater comfort and flexibility.

FIG. 16 illustrates another form of the neural stent 6 of the present invention wherein top and bottom axially elongated members 72, 70 which are generally U-shaped in transverse cross-section are joined together to define the neural stent with an overall generally cylindrical shape having an axial bore 10 extending between the top and bottom elongated members. In this particular embodiment shown in FIG. 16, the bottom elongated member 70 includes opposite lateral edges 76 which define a channel 86 in each for receiving the opposite lateral edges 80 of the top elongated member 72 by sliding the top elongated member into the channels 86 of the bottom elongated member, or by snap-fitting the top elongated member 72 into the channels 86 of the bottom elongated member 70 to secure the two members together to define the neural stent 6. Also, in this particular embodiment shown in FIG. 16, it can be seen that the top and bottom elongated members 72, 70 may include a plurality of openings 16 formed through the thickness thereof to allow fluid flow into and out of the axial bore 10 which houses and protects the median nerve 2 of the patient. Again, FIG. 16 shows that the neural stent 6, and in particular, the top and bottom elongated members 72, 70 thereof, may be bowed or arched to provide greater flexibility and comfort to the patient in whom the neural stent is implanted.

FIG. 17 illustrates another form of the neural stent 6 of the present invention which is similar in many respects to the stents shown in FIGS. 15 and 16. In this particular embodiment shown in FIG. 17, the bottom axially elongated member 70 is U-shaped or C-shaped to define a channel 64 for receiving the median nerve 2 of a patient, and the top elongated member 72 is formed as a plurality of slightly arched or bowed, individual pieces 74 to allow the neural stent to be assembled in situ during implantation in the patient's wrist or other location to protect the injured nerve. Each piece 74 of the top elongated member 72 includes an opening 16 formed through the thickness thereof to allow fluid flow therethrough into the bore 10 formed by the top and bottom members where the median nerve 2 is situated. Also, the individual pieces 74 forming the top elongated member 72 may have opposite lateral concave-shaped (one or both)-sides 88 so that adjacent pieces 74 only touch one another near their other opposite sides (i.e., lateral edges 80) to define a gap 90 between adjacent pieces. The gaps 90 provided by this structure will allow fluid to flow to the median nerve 2 situated within the axial bore 10 of the neural stent 6. Each piece 74 of the top elongated member 72 may have lateral edges 80 formed in a similar manner to that shown and described for the top elongated members 72 of the stents shown in FIGS. 15 and 16, and similarly, the bottom elongated member 70 may have lateral edges 76 with the same or similar structure as that of the lateral edges 76 of the bottom elongated members 70 shown and described in relation to the neural stent of FIGS. 15 and 16 so that the top elongated member 72 may be snap-fitted to or slidably received by the bottom elongated member 70 to secure the top and bottom members of the neural stent together.

It should be realized that the particular shape of the L-shaped flanges 78 of the bottom elongated members 70 may be interchanged with that of the complementary L-shaped flanges 82 of the top elongated members 72 of the neural stents 6 shown in FIGS. 15-17, or alternatively other configurations may be suitable for use, in order to secure the top elongated member 72 to the bottom elongated member 70 of the neural stents of the present invention.

Figure 18:
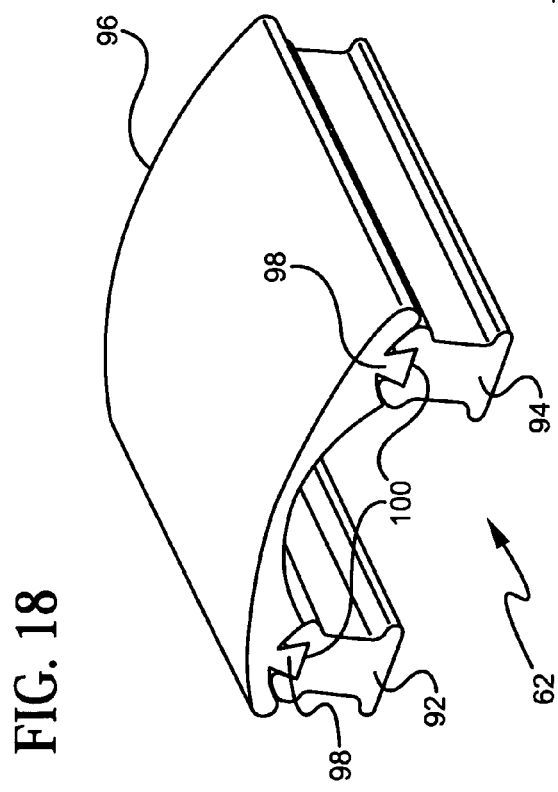
FIG. 18 is a perspective view of a device for treating a patient having carpal tunnel disease or other nerve injury formed in accordance with a seventh form of the present invention.

The neural stent or shield 62 formed in accordance with another form of the present invention is illustrated by FIG. 18 of the drawings. As shown in FIG. 18, the neural shield 62 includes a first elongated member 92 and a second elongated member 94 situated in parallel with the first elongated member 92 and spaced apart therefrom. The neural shield 62 includes a bridging member 96 interposed between and mountable to the first and second elongated members 92, 94. The first and second elongated members 92, 94 and the bridging member 96 together define a channel 64 for receiving and protecting the median nerve 2 of a patient. The bridging member 96, which may be arched or bowed, is situated under the carpal ligament 4 where the neural shield 62 is implanted in a patient being treated for carpal tunnel syndrome. The bridging member 96 supports and separates the carpal ligament 4 from the median nerve 2 which is protected by the neural shield in the channel 64. The bridging member 96 may be a solid piece, or may be formed from a mesh or include a plurality of openings formed through its thickness to allow the flow of fluids to reach the median nerve 2 situated within the channel 64.

Like the embodiments shown in FIGS. 15-17, the neural shield 62 of the present invention illustrated by FIG. 18 may be assembled in situ during its surgical implantation. The bridging member 96 of the neural shield 62 includes an inner surface facing the channel 64 from which extends outwardly a pair of spaced apart, parallel rails 98 which are preferably dovetailed in transverse cross-sectional shape. The top edges of the first and second elongated members 92, 94 include grooves or recesses 100 formed therein which have a complementary dovetail shape in transverse cross-section so as to selectively receive the projections or rails 98 of the bridging member 96. It is, of course, envisioned to be within the scope of the present invention to reverse the positions of the rails 98 and recesses 100 so that the elongated members 92, 94 include the projecting rails 98 and the bridging member 96 includes the rail receiving recesses 100.

During implantation of the neural shield 62 of the present invention shown in FIG. 18, the first and second elongated members 92, 94 are positioned on opposite lateral sides of the median nerve 2, and the bridging member 96 is situated above the first and second members 92, 94 and between the transverse carpal ligament 4 and the median nerve 2, with its rails 98 being snap-fitted into or slidably received by the respective recess 100 formed in each of the first and second elongated members 92, 94 to secure the bridging member 96 to the first and second elongated members.

Figure 19:
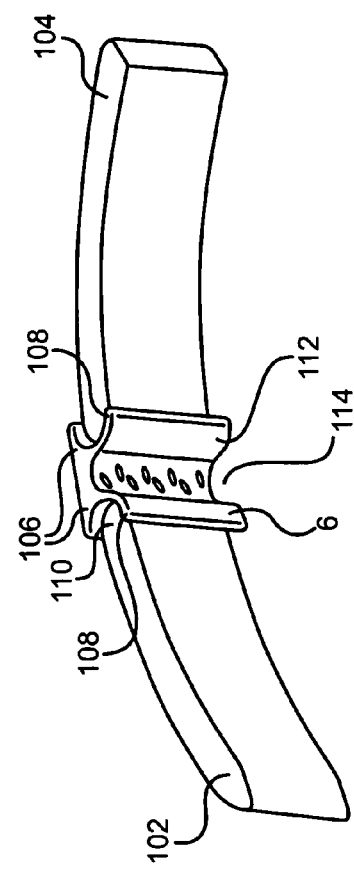
FIG. 19 is a perspective view of a device for treating a patient having carpal tunnel disease formed in accordance with an eighth form of the present invention, which is suitable for use when the carpal ligament is transected.

There may be occasions where the physician requires under the circumstances that the carpal ligament 4 be severed or transected to provide complete relief to the patient suffering from carpal tunnel disease. FIG. 19 illustrates a device for use in treating carpal tunnel syndrome where the carpal ligament is transected during surgery. One of the problems with transecting the carpal ligament is that the severed ends may contact the median nerve 2 and cause irritation and injury to the nerve. Accordingly, and as shown in FIG. 19, the device of the present invention, in this particular embodiment, includes a first bridging member 102 which is positionable under the first section of a transected carpal ligament, and a second bridging member 104 which is positionable under the second section of the transected carpal ligament. The device further includes a neural stent 6 which is interposed between and joined to the first and second bridging members 102, 104. The neural stent 6 has opposite lateral sides 106 in which are formed grooves 108 for receiving facing ends 110 of the first and second bridging members 102, 104. The neural stent 6 also has a lower surface 112 in which a channel 114 is formed for receiving and protecting the median nerve 2 of the patient. The median nerve 2 which is situated within the channel 114 is protected from coming in contact with the transected ends of the carpal ligament 4 when the device is implanted in a patient.

Another device of the present invention for treating carpal tunnel disease when the carpal ligament must be transected is shown in FIGS. 20-24 of the drawings. The device includes a first clamping member 116 having a lower jaw 118 and an upper jaw 120 overlying and aligned with the lower jaw 118. The lower jaw 118 and the upper jaw 120 of the first clamping member 116 are positionable at a first portion 122 of a carpal ligament 4, with the first portion 122 of the carpal ligament being interposed therebetween. The upper jaw 120 and the lower jaw 118 are clamped together and engage the first portion 122 of the carpal ligament to secure the first portion therebetween when the device is implanted in a patient being treated for carpal tunnel syndrome.

Similarly, the device includes a second clamping member 124. The second clamping member 124 includes a lower jaw 126 and an upper jaw 128 overlying and aligned with the lower jaw 126. The lower jaw 126 and the upper jaw 128 of the second clamping member 124 are positionable at a second portion 130 of the carpal ligament, with the second portion 130 of the carpal ligament being interposed therebetween. The lower jaw 126 and the upper jaw 128 engage and clamp the second portion 130 of the carpal ligament 4 and secure the second portion therebetween during implantation of the device.

To tightly clamp the upper and lower jaws of the first and second clamping members 116, 124 together, the upper face of the lower jaw 118, 126 of each clamping member may include one or more openings 132 formed therein, and the lower face of the upper jaw 120, 128 of each clamping member may include bulbous projections 134 which are aligned with and received by the openings 132 of the lower jaw, although it is envisioned to be within the scope of the present invention to reverse the locations of the openings 132 and bulbous projections 134 on the upper and lower jaws of each clamping member. With the carpal ligament situated between the upper and lower jaws of each clamping member 116, 124, the upper and lower jaws 120, 118, 128, 126 are press fitted together so that the bulbous projections 134 resiliently snap into the openings 132 to secure the upper and lower jaws together with the carpal ligament 4 clamped therebetween, as shown in FIGS. 21 and 22 of the drawings.

The device of the present invention shown in FIGS. 20-24 further includes an elastic bridge member 136 situated between and connected to the first clamping member 116 and the second clamping member 124. The bridge member 136 may include a plurality of elastic and flexible sutures 138 or other means for elastically interconnecting the two clamping members together. As shown in FIG. 20, the plurality of elastic sutures 138 preferably criss-cross one another and extend between the lower jaws 118, 126 of the first and second clamping members 116, 124.

After the carpal ligament 4 is clamped between the first and second clamping members 116, 124, as shown in FIG. 22, it is surgically transected, with the middle portion 140 of the ligament which extends between the first and second clamping members being removed. Thus, the ends of the transected ligament sections are secured and preferably covered by the first and second clamping members 116, 124, as shown in FIG. 23. The device then springs open, extending the ligament's is length once the ligament is severed, as shown in FIG. 24. The elasticity of the crisscrossing sutures 138 bridging the first and second clamping members 116, 124 provide flexibility and movement to the patient's wrist, and support and stability for the patient's hand. In the expanded state, the device provides clearance for the median nerve 2 beneath the ligament.

In yet another form of the present invention, and as shown in FIG. 25 of the drawings, a device for treating a patient suffering from carpal tunnel syndrome includes a first flexible rod 142 and a second flexible rod 144. Each of the first and second flexible rods 142, 144 has a diameter which is greater than that of the median nerve 2. The first and second flexible rods 142, 144 are implanted in a patient on opposite lateral sides of the median nerve 2 and extend in the same longitudinal direction as the median nerve in order to separate the carpal ligament 4 from the median nerve 2. The flexible rods 142, 144 may be hollow tubes or may be solid, and preferably have a length of about 0.5 centimeters to about 3.0 centimeters. The rods 142, 144 are inserted parallel to the nerve just below the transverse carpal ligament. Preferably, the rods 142, 144 have a diameter which is about 3 millimeters to about 6 millimeters, which is slightly greater than the diameter of the median nerve 2. Alternatively, the rods 142, 144 may be tapered with a gradual increase in diameter from the forward end thereof which is first inserted under the carpal ligament toward the opposite rearward end thereof which is held or manipulated by the surgeon. Once adequate release of pressure on the median nerve is obtained at a certain diameter of the rods 142, 144, advancement of the rods would stop and excess rod may be snapped or cut off. Thus, the rods 142, 144 protect the median nerve 2 against compression caused by the transverse carpal ligament 4. The rods 142, 144 preferably have a highly smooth surface so as not to irritate the nerve or tendons and ligaments. The outer surface of the rods may be coated with a non-irritant substance, such as polytetrafluoroethylene, which is also commonly referred to as Teflon™ or PTFE.

In an alternative form of the present invention and as a variation of the embodiments shown in FIG. 25, each rod or tube may be in the form of an elongated sack 146 defining a pocket 148 therein, as shown in FIG. 26 of the drawings. Preferably, the pocket 148 is at least partially filled with a hydrogel or silicone and the sacks 148, like the rods 142, 144 of FIG. 25, preferably have an outer surface which is coated with a non-irritant substance, such as polytetrafluoroethylene.

As is evident from the foregoing description of the various embodiments of the present invention, a device for treating carpal tunnel disease or other nerve damage may be implanted in a patient to protect a nerve, such as the median nerve, from compression by nearby tissue, bone or ligaments, such as the transverse carpal ligament. The device and methods for implanting such a device, in accordance with the present invention, avoid the complications and detrimental effects associated with known surgical procedures for treating carpal tunnel syndrome. The device may be easily implanted in a patient's body to allow the median nerve to heal and return to function without the need to cut the transverse carpal ligament. However, embodiments of the present invention provide protection for the median nerve and support and stability for the patient's hand should it be required to transect the transverse carpal ligament.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A device for treating a patient having an injury to or inflammation of a nerve, which comprises:
   a neural stent, the neural stent being at least generally in the form of a cylindrical tube and having a tubular body, the tubular body having a bore formed axially therethrough for receiving and protecting an inflamed or injured nerve;
   wherein the tubular body of the neural stent includes an outer wall for at least partially surrounding an inflamed or injured nerve, and a slot formed through the thickness of the outer wall and extending axially there along, the slot being in communication with the bore for receiving through the slot and into the bore the inflamed or injured nerve; and
   a rigid delivery envelope, the envelope having a top wall and a bottom wall opposite the top wall, the top and bottom walls defining therebetween a pocket for housing the neural stent when the stent has a generally planar rectangular form and is in the first shape, the rigid delivery envelope further having an open end formed by the top and bottom walls and defining an opening communicating with the pocket through which the neural stent may pass.

2. A device for treating a patient having an injury to or inflammation of a nerve as defined by claim 1, wherein the stent is formed at least partially from a material absorbable by a patient's body.

3. A device for treating a patient having an injury to or inflammation of a nerve as defined by claim 1, wherein the neural stent is formed at least partially from a material which is non-absorbable by a patient's body.

4. A device for treating a patient having an injury to or inflammation of a nerve as defined by claim 1, wherein the tubular body of the neural stent includes an outer wall formed as a mesh to allow the passage of fluids therethrough and into the axial bore of the neural stent.

5. A device for treating a patient having an injury to or inflammation of a nerve as defined by claim 1, wherein the tubular body of the neural stent includes an outer wall, the outer wall having a plurality of openings formed through the thickness thereof, the openings communicating with the axial bore to allow the passage of fluids through the openings and into the axial bore.

6. A device for treating a patient having an injury to or inflammation of a nerve as defined by claim 1, wherein the tubular body of the neural stent includes a main body portion, a first open axial end and a second open axial end situated opposite the first open axial end, the main body portion being interposed between the first open axial end and the second open axial end, at least one of the first open axial end and the second open axial end being flared to have a diameter which is greater than that of the main body portion of the neural stent.

7. A device for treating a patient having an injury to or inflammation of a nerve as defined by claim 1, wherein the neural stent is formed of an elastically deformable material, the neural stent being deformable between a generally cylindrical first shape and a second shape which is different from the first shape.

8. A device for treating a patient having an injury to or inflammation of a nerve, which comprises:
   a neural stent, the neural stent being at least generally in the form of a cylindrical tube and having a tubular body, the tubular body having a bore formed axially therethrough for receiving and protecting an inflamed or injured nerve;
   wherein the neural stent is formed of an elastically deformable material, the neural stent being deformable between a first shape in which the neural stent is in a generally planar rectangular form having opposite lateral edges, and a second shape in which the neural stent is in a generally cylindrical form and where the lateral edges of the material face each other and define therebetween a slot communicating with the axial bore, the tubular body having a length extending between a first end and a second end thereof, and the slot extending the length of the tubular body; and
   a rigid delivery envelope, the envelope having a top wall and a bottom wall opposite the top wall, the top and bottom walls defining therebetween a pocket for housing the neural stent when the stent has a generally planar rectangular form and is in the first shape, the rigid delivery envelope further having an open end formed by the top and bottom walls and defining an opening communicating with the pocket through which the neural stent may pass.

9. A device for treating a patient having an injury to or inflammation of a nerve as defined by claim 1, wherein the neural stent is formed from a deformable material having shape memory properties, the neural stent being deformable between a first shape wherein the neural stent has a generally cylindrical form, and a second shape which is different from the first shape.

10. A device for treating a patient having an injury to or inflammation of a nerve, which comprises:
    a neural stent, the neural stent being at least generally in the form of a cylindrical tube and having a tubular body, the tubular body having a bore formed axially therethrough for receiving and protecting an inflamed or injured nerve;
    wherein the neural stent is formed from a deformable material having shape memory properties, the neural stent being deformable between a first shape in which the neural stent is in a generally planar form having opposite lateral edges, and a second shape in which the neural stent is in a generally cylindrical form and where the lateral edges of the material face each other and define therebetween a slot communicating with the axial bore the tubular body having a length extending between a first end and a second end thereof, and the slot extending the length of the tubular body; and
    a rigid delivery envelope, the envelope having a top wall and a bottom wall opposite the top wall, the top and bottom walls defining therebetween a pocket for housing the neural stent when the stent has a generally planar rectangular form and is in the first shape, the rigid delivery envelope further having an open end formed by the top and bottom walls and defining an opening communicating with the pocket through which the neural stent may pass.

11. A device for treating a patient having an injury to or inflammation of a nerve as defined by claim 1, wherein the neural stent includes a first axial end and a second axial end opposite the first axial end, and wherein the device further includes an anchor for attaching the stent to the patient's body when the device is being implanted in the patient's body, the anchor being affixed to and extending axially from at least one of the first axial end and the second axial end.

12. A device for treating a patient having an injury to or inflammation of a nerve, which comprises:
    a neural stent, the neural stent being at least generally in the form of a cylindrical tube and having a tubular body, the tubular body having a bore formed axially therethrough for receiving and protecting an inflamed or injured nerve;
    wherein the tubular body of the neural stent includes an outer wall, the outer wall having an outer surface and an inner surface opposite the outer surface and facing the axial bore for receiving the inflamed or damaged nerve, the inner surface being lubricious to allow movement of the nerve within the bore, the tubular body having a length extending between a first end and a second end thereof;
    a slot formed through the outer wall of the tubular body and being in communication with the bore for receiving through the slot and into the bore the inflamed or injured nerve; and
    a rigid delivery envelope, the envelope having a top wall and a bottom wall opposite the top wall, the top and bottom walls defining therebetween a pocket for housing the neural stent when the stent has a generally planar rectangular form and is in the first shape, the rigid delivery envelope further having an open end formed by the top and bottom walls and defining an opening communicating with the pocket through which the neural stent may pass.

13. A device for treating a patient having an injury to or inflammation of a nerve as defined by claim 12, wherein the neural stent includes a plurality of tissue anchors formed thereon.

14. A device for treating a patient having an injury to or inflammation of a nerve as defined by claim 13, wherein the tissue anchors include barbs extending outwardly from the outer surface of the neural stent outer wall.

15. A device for treating a patient having an injury to or inflammation of a nerve as defined by claim 8, further comprising at least one tissue anchor joined to the tubular body and being extendible axially beyond one of the first and second ends of the tubular body.

* * * * *